(12) United States Patent
Kent

(10) Patent No.: US 10,524,762 B2
(45) Date of Patent: Jan. 7, 2020

(54) FETAL HEARTBEAT PHANTOM

(71) Applicant: Government of the United States as represented by the Secretary of the Air Force, Wright-Patterson AFB, OH (US)

(72) Inventor: Zackary J. Kent, Edwards, CO (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 218 days.

(21) Appl. No.: 15/815,000

(22) Filed: Nov. 16, 2017

(65) Prior Publication Data
US 2019/0142369 A1    May 16, 2019

(51) Int. Cl.
*G09B 23/28* (2006.01)
*A61B 8/08* (2006.01)
(Continued)

(52) U.S. Cl.
CPC .......... *A61B 8/0866* (2013.01); *A61B 5/0444* (2013.01); *A61B 8/02* (2013.01);
(Continued)

(58) Field of Classification Search
USPC .......................... 434/262, 267, 268, 272, 273
See application file for complete search history.

(56) References Cited

U.S. PATENT DOCUMENTS

| 5,374,194 A | * | 12/1994 | Walcerz | G09B 23/288 |
| | | | | 434/265 |
| 6,205,871 B1 | * | 3/2001 | Saloner | B33Y 80/00 |
| | | | | 73/866.4 |

(Continued)

FOREIGN PATENT DOCUMENTS

| WO | 2006051531 | 5/2006 |
| WO | 2007010534 | 1/2007 |

(Continued)

OTHER PUBLICATIONS

Cirs Inc., "Female Ultrasound Training Pelvis: Model 404A," Datasheet [online] (copyright 2013), retreived on Sep. 26, 2017 from <URL: http://www.cirsinc.com/file/Products/404A/404A%20DS%20032916.pdf>.

(Continued)

*Primary Examiner* — Kurt Fernstrom
(74) *Attorney, Agent, or Firm* — AFMCLO/JAZ; Chastity Whitaker

(57) ABSTRACT

A phantom for simulating fetal heartbeat. The phantom includes a housing and a fetal heartbeat simulator. The housing has an exterior shaped like a female human pelvic region and surrounds an interior. The fetal heartbeat simulator includes a tube having a proximal end and a distal end, the distal end being positioned within the interior of the housing. The tube is filled with a first fluid having a first compressibility. A second fluid, having a compressibility that is greater than the compressibility of the first fluid, is disposed at the distal end of the tube. A pressure mechanism (Continued)

operably coupled to the proximal end of the tube is configured to selectively compress and decompress the first and second fluids.

18 Claims, 6 Drawing Sheets

(51) Int. Cl.
  *A61B 5/0444* (2006.01)
  *A61B 8/02* (2006.01)
  *A61B 8/00* (2006.01)
  *A61B 5/00* (2006.01)
  *G16H 50/50* (2018.01)

(52) U.S. Cl.
  CPC ............ *A61B 8/587* (2013.01); *G09B 23/281* (2013.01); *G09B 23/286* (2013.01); *A61B 5/4362* (2013.01); *G16H 50/50* (2018.01)

(56) References Cited

U.S. PATENT DOCUMENTS

| | | | | |
|---|---|---|---|---|
| 6,461,165 | B1* | 10/2002 | Takashina | G09B 23/288 434/262 |
| 6,790,043 | B2* | 9/2004 | Aboud | G09B 23/303 434/262 |
| 7,510,398 | B1* | 3/2009 | Thornton | G09B 23/288 434/262 |
| 8,538,776 | B2 | 9/2013 | Reiner | |
| 8,586,932 | B2 | 11/2013 | Rousso et al. | |
| 9,183,763 | B2* | 11/2015 | Carson | G09B 23/288 |
| 10,229,615 | B2* | 3/2019 | Carson | G09B 23/288 |
| 2003/0220718 | A1* | 11/2003 | Jaszczak | G01R 33/58 700/282 |
| 2004/0033477 | A1* | 2/2004 | Ramphal | G09B 23/306 434/272 |
| 2004/0126746 | A1* | 7/2004 | Toly | G09B 23/28 434/262 |
| 2008/0042067 | A1 | 2/2008 | Rousso et al. | |
| 2008/0131855 | A1 | 6/2008 | Eggert | |
| 2009/0226867 | A1* | 9/2009 | Kalafut | G09B 23/32 434/268 |
| 2010/0227303 | A1 | 9/2010 | Deering | |
| 2012/0034586 | A1* | 2/2012 | Gomo | G09B 23/28 434/265 |
| 2015/0024362 | A1* | 1/2015 | Feins | G09B 23/303 434/268 |

FOREIGN PATENT DOCUMENTS

| | | |
|---|---|---|
| WO | 2008010227 | 1/2008 |
| WO | 2012122462 | 9/2012 |

OTHER PUBLICATIONS

Kyoto Kagaku Co., "US-7a: Fetus Ultrasound Examination Phantom 'Space Fan-St,'" p. 58 of Product Catalog [online] (2016), retrieved on Sep. 26, 2017 from <URL: https://www.kyotokagaku.com/products/detail03/pdf/us-7a_catalog.pdf>.

Kyoto Kagaku Co., "Female Pelvic Ultrasound Phantom," Product Page [online] (copyright 1999-2012), retrieved from <URL: https://www.kyotokagaku.com/products/detail03/us-10.html>.

Cae Healthcare, Pioneering Ultrasound Training Solutions, pp. 31-44 of Product Catalog [online] (2016), retrieved on Sep. 26, 2017 from <URL: https://caehealthcare.com/ultrasound-simulation>.

* cited by examiner

FETAL HEARTBEAT PHANTOM

RIGHTS OF THE GOVERNMENT

The invention described herein may be manufactured, used, and licensed by or for the Government of the United States for all governmental purposes without the payment of any royalty.

FIELD OF THE INVENTION

This invention relates to the field of radiology. More particularly, this invention relates to an apparatus for radiological training using clinical equipment designed for use with patients.

BACKGROUND OF THE INVENTION

Early determination of pregnancy can be very important to the health and well-being of a woman. For example, knowing that she is pregnant, a woman can make life-style adjustments that will protect her own health as well as that of her unborn child, such as stopping smoking and drinking, changing dietary choices, and so forth.

While various home pregnancy tests are available to help with the determination of pregnancy, it is typically considered prudent to have positive results confirmed by a health care professional. One way that health care professionals determine pregnancy is by detecting the presence of a fetus with radiological testing, such as ultrasound. Diagnostic ultrasound operates by directing high frequency sound waves (ranging from about 2 MHz to about 9 MHz) into the body of a patient using a probe, e.g., an ultrasound transducer. Certain transducers also detect echoes received from the reflection of the sound waves at tissue interfaces, the relative strength and other characteristics of such echo being measured. Variations in these echoes are created by the differing densities of the tissues and structures. A sonographic image is produced by depicting representations of the echo variations.

Because a fetus is very small at the time when a pregnancy might be first suspected, the fetus may be very difficult to detect unless the health care professional has some degree of experience with both the procedure that is conducted and the particular ultrasound equipment that is used. In addition to the requisite technical expertise, the health care professional must also be sensitive to the needs of the patient, as the determination of pregnancy and the intimacy of the examination tend to affect the patient's emotional state.

Therefore, it is well for the health care professional to train such that the technical aspects of ultrasound may be performed with ease. One device developed to facilitate such training is a radiological phantom, which are manufactured, anatomical replicas—to a greater or lesser extent—of a portion of the patient to be examined.

Unfortunately, conventional phantoms for gynecological or obstetric procedures only work with transducers or other equipment that is specifically designed and dedicated for use with the phantom and not suitable or approved for in vivo examination. While the health care professional is able to gain some experience using such conventional phantoms, the experience is limited because the same equipment is not necessarily used during in vivo examination. Some of these phantoms are extremely complex and require a level of maintenance that is not practical for some training environments. Further, some phantoms are extremely expensive, and thus are cost prohibitive to some facilities.

What is needed, therefore, is an ultrasound phantom that reduces issues such as those represented above, at least in part.

SUMMARY OF THE INVENTION

The present invention overcomes the foregoing problems and other shortcomings, drawbacks, and challenges of training medical practitioners in the early detection of pregnancy by way of ultrasound examination. While the invention will be described in connection with certain embodiments, it will be understood that the invention is not limited to these embodiments. To the contrary, this invention includes all alternatives, modifications, and equivalents as may be included within the spirit and scope of the present invention.

According to an embodiment of the present invention, a phantom for simulating fetal heartbeat includes a housing and a fetal heartbeat simulator. The housing has an exterior shaped like a female human pelvic region and surrounds an interior. The fetal heartbeat simulator includes a tube having a proximal end and a distal end, the distal end being positioned within the interior of the housing. The tube is filled with a first fluid having a first compressibility. A second fluid, having a compressibility that is greater than the compressibility of the first fluid, is disposed at the distal end of the tube. A pressure mechanism operably coupled to the proximal end of the tube is configured to selectively compress and decompress the first and second fluids.

Other embodiments of the present invention are directed to a phantom for simulating fetal heartbeat. The phantom includes a housing and a fetal heartbeat simulator. The housing has an exterior shaped like a female human pelvic region and surrounds an interior. A fetal structure is positioned within the interior of the housing. The fetal heartbeat simulator includes a tube having a proximal end and a distal end, the distal end being operably coupled to the fetal structure within the interior of the housing. The tube is filled with a first fluid having a first compressibility. A second fluid, having a compressibility that is greater than the compressibility of the first fluid, is disposed at the distal end of the tube. A pressure mechanism operably coupled to the proximal end of the tube is configured to selectively compress and decompress the first and second fluids.

In various embodiments according to this aspect of the invention, the fetal structure may be substantially the size of an eight-week-old human fetus. In some embodiments, the first fluid is air and the second fluid is water. In some embodiments, the pressure mechanism is a hand-operated pressure bulb. In some embodiments, the pressure mechanism is a reciprocating pump with a rate controller. In some embodiments, a uterus structure is disposed within the interior and encases the fetal structure. In some embodiments, a bladder structure is disposed within the interior. In some embodiments, a bowel structure is disposed within the interior. In some embodiments, a channel opening extends from the exterior to the interior for accommodating such things as an ultrasound probe.

According to another aspect of the invention, a method of training a health care professional using the fetal heartbeat phantom includes actuating the pressure mechanism to simulate a fetal heartbeat. An ultrasound transducer is operated on the exterior of the phantom such that the selective compression and decompression of the first and second fluids may be detected.

Thus, a phantom according to various embodiments of the present invention represents a significant improvement to the art, in that it provides a representation of fetal heart activity that may be observed and used by a health care professional in training to refine their skills. This allows for a broader range of clinical scenarios to be addressed with the phantom, as well as more advanced training with the ultrasound equipment that will actually be used in the clinical setting.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 1:
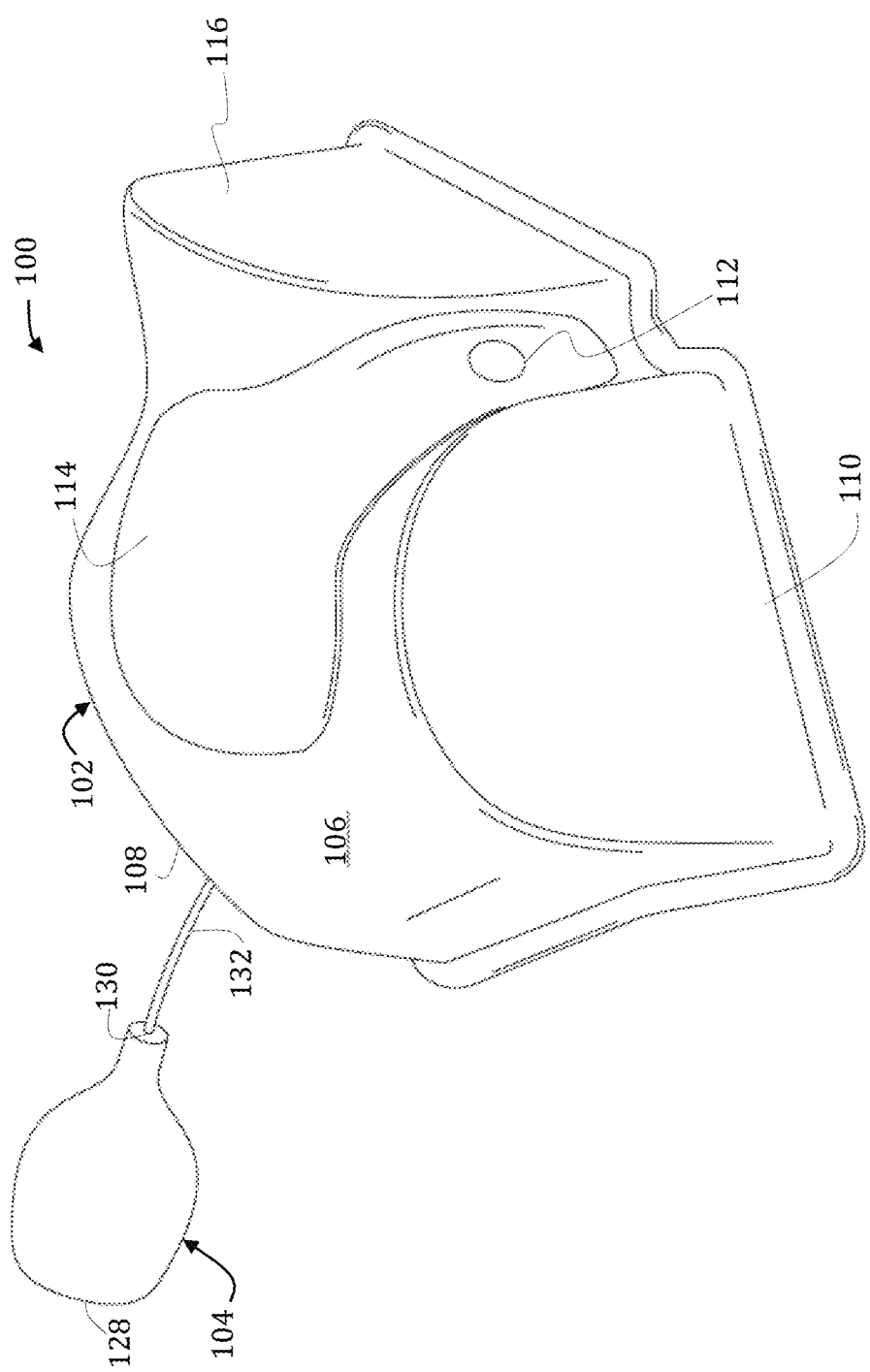
FIG. 1 is side elevational view of an ultrasound phantom according to an embodiment of the present invention.
Figure 2:
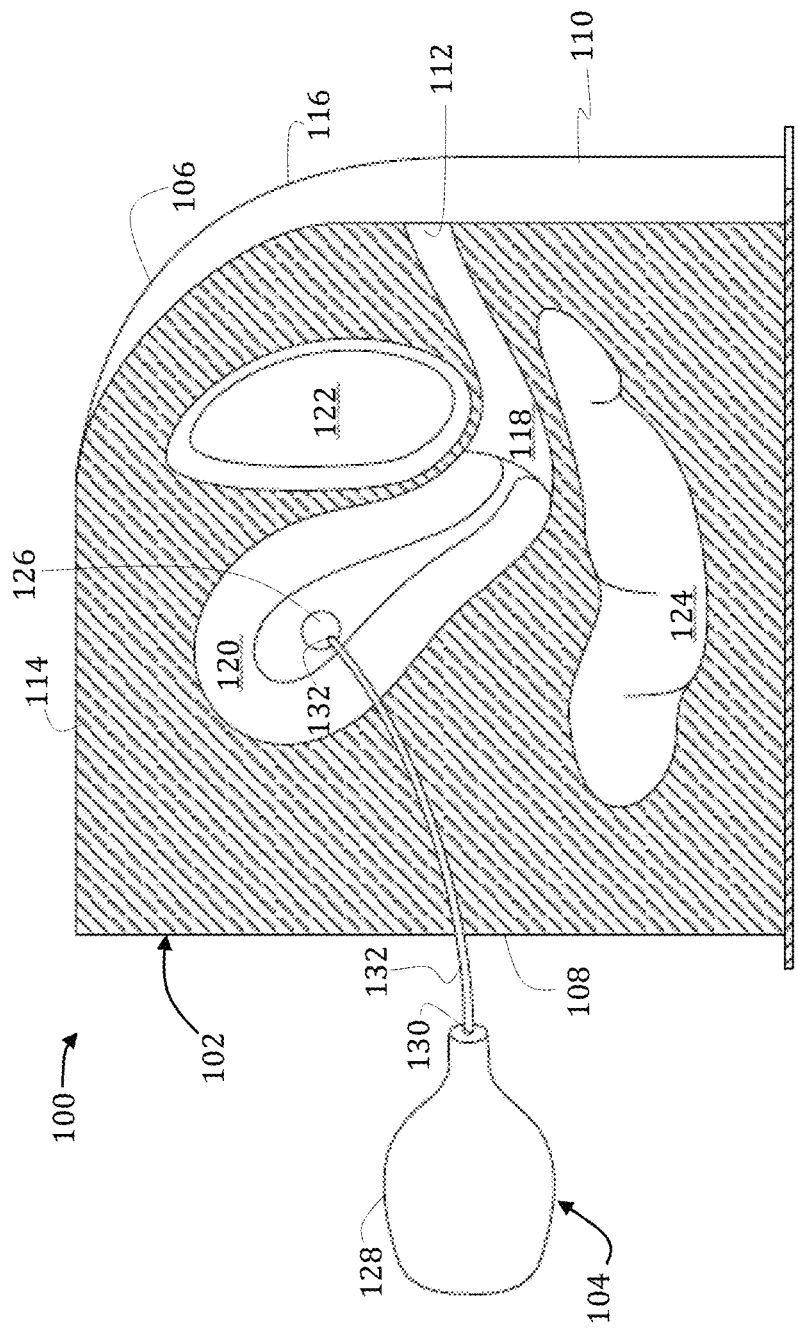
FIG. 2 is a sagittally-directed, cross-sectional view of the ultrasound phantom of FIG. 1.
Figure 3:
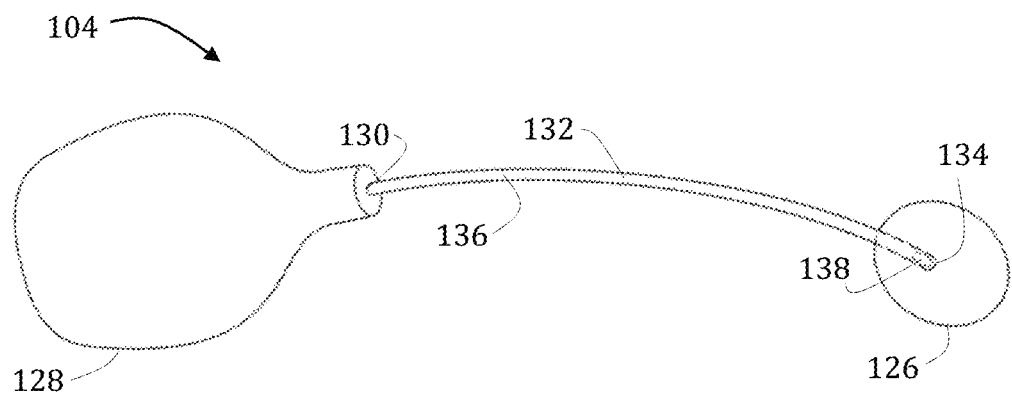
FIG. 3 is a side elevational view of a fetal heartbeat simulator according to an embodiment of the present invention.

Turning now to the figures, and in particular to FIGS. 1-3, there is depicted an external view of a phantom 100 according to an embodiment of the present invention. Generally, the phantom 100 includes a housing 102 and a fetal heartbeat simulator 104. An exterior 106 of the housing 102 of the phantom 100 may be shaped and sized to generally approximate the pelvic region of an adult woman in a supine position. In some embodiments, a superior end 108 of the housing 102 may extend to approximately the floating rib region of a woman. In some embodiments, the inferior end 110 of the housing 102 may extend into a mid-thigh region of a woman. The housing 102, in some embodiments, may include orifice 112 that is disposed in a region corresponding to the vaginal orifice.

The housing 102 may be constructed of various materials according to a desired embodiment. For example, in some embodiments the housing 102 may be constructed with a replaceable section 114 formed of one type of material and an encasing section 116 formed of another type of material. As illustrated herein and for obstetric training, the replaceable section 114 may include structures simulating certain anatomy for examination, land marking, or both. Exemplary structures may include as a vaginal canal 118, a uterus 120, a bladder 122, an intestine 124, a fetus 126, and so forth. In this manner, one or more replaceable sections 114 may be used with the same encasing section 116 for simulating various anatomical or diseased states, as described in greater detail below.

The exemplary structures of the replaceable section 114 may be constructed from enclosures filled, wholly or partially, with one or more fluids. The exemplary structures may be surrounded by fluid or supported by a polymeric or other material. The presence of fluid within and surrounding these organ structures may result in more representative images when using ultrasound. Likewise, in some embodiments, the organ structures may be fashioned with materials with different density characteristics so as to be distinguishable when using ultrasound equipment.

For example, in some embodiments the bladder structure 122 may be a thin-walled (polymeric, expanded foam, and so forth) structure that is filled with a fluid such as water. In some embodiments, the uterus structure 120 may be a thick-walled (polymeric, expanded foam, and so forth) structure of a relatively dense material that may be likewise filled with a fluid. In some embodiments, the intestine structure 124 may be a relatively thin-walled structure surrounding a fluid, such as water or saline. In some embodiments, the housing 102 may be formed of a material that is relatively denser than the uterus structure 120. Fluids and other materials may also include antimicrobial agents to extend the shelf life of the phantom 100.

The fetus 126 may be an ovate solid structure of a suitable material to provide the appropriate, relative ultrasound contrast. In some embodiments, the fetus 126 may be formed of a material that is denser than the uterus structure 120, or with a suitable contrast enhancing agent incorporated into the material.

The encasing section 116 may be configured to receive and support the replaceable section 114 such that anatomical landmarks of the replaceable section 114 align with the anatomical landmarks of the encasing section 116. The encasing section 116 may, like the replaceable section 114, include anatomical structures configured to more accurately simulate in vivo conditions. While not specifically illustrated herein, exemplary anatomical structures may include materials to simulate bone (such as the vertebral column or ilium), vasculature (such as the descending aorta or femoral arteries/veins), musculature (such as the psoas, the abductors, or the adductors), and so forth.

Materials used in constructing phantom 100 may be further selected or selectively treated to resist or reduce contamination and degradation considering the intended environments of use.

Referring still to FIGS. 1-3, the fetal heartbeat simulator 104 of the phantom 100 is described in greater detail. The fetal heartbeat simulator 104 includes a pressure mechanism (illustrated in these figures as a pressure bulb 128) operably coupled to a proximal end 130 of a tube 132 (such as a 6 Fr catheter). A distal end 134 of the tube 132 may be configured to be received by, or operably coupled to, the fetus 126, if present. While FIG. 2 illustrates the pressure bulb 128 as being external to the housing 102, it would be readily understood that such construction is not limiting. In fact, in some instances the pressure mechanism may be incorporated into the housing 102 so as to create a unitary phantom structure. In other embodiments, the pressure mechanism may be mounted to the exterior 106 of the housing 102.

As shown in greater detail in FIG. 3, the tube 114 may be sealed at the distal end 134 and be filled with at least two fluids 136, 138 with the second fluid 138 (represented as a bubble) being restricted to the distal end 134 of the tube 132.

According to some embodiments, the bubble of the second fluid 138 may be maintained at the distal end 134 of the tube 132 solely by gravity. In other embodiments, one or more of a mesh, a permeable membrane, or other such material may be disposed near the distal end 134 of the tube 132 so as to retain the bubble of the second fluid 138 at or near the distal end 134 of the tube 132. In other embodiments, surface tension or other similar property difference between the first and second fluids 136, 138 may to maintain the distal position of the second fluid 138.

The first fluid 136 may contact, surround, or otherwise be disposed proximally to the second fluid 138. In some embodiments, the first and second fluids 136, 138 interact such that a pressure force exerted (or released) on the first fluid 136 causes a compression or decompression (respectively) in the second fluid 138. Generally, the second fluid 138 is more compressible than the first fluid 136 such that when a force is applied to the first fluid 136 via the pressure bulb 128, the force is transferred thru the first fluid 136 to the second fluid 138. In other embodiments, the second fluid 138 may be less compressible than the first fluid 136.

In some embodiments, the first fluid 136 may be a liquid (such as water or saline) and the second fluid 138 may be a gas (such as air). Some embodiments may further include a third fluid (not shown), wherein the third fluid is primarily located within the pressure bulb 128, the tube 132 primarily filled with the first fluid 136, and the bubble of the second fluid 128 remains positioned within the distal end 134 of the tube 132. The suitable third fluid may be a gas.

In use, and by selectively manually or mechanically squeezing and releasing the pressure bulb 128, the compressive force applied to the pressure mechanism 128 is transferred through the first fluid 136 to the bubble of the second fluid 138 at the distal end 134 of the tube 132 such that the bubble selectively expands and contracts, respectively. This slight motion of the interface between the first and second fluids 136, 138 creates a very faint sound that mimics the heartbeat of a vital fetus. This expansion and contraction, when measured with ultrasound, may be used to simulate the cardiac activity of a fetus. That is, the ultrasound detects the interface between the first fluid 136 and second fluid 138 in tube 132 when actuated by the pressure bulb 128 and images the activity as it would a fetal heartbeat. By increasing or decreasing the frequency of the compression and decompression cycles, a rate of the apparent fetal heartbeat may be increased and decreased to simulate the fetus (with normal fetal heartbeat ranging from about 110 beats per minute to about 160 beats per minute and is related to fetal maturity level). For example, a fetus of seven-to-eight weeks may be simulated in this manner so that a health care professional can practice finding faint heartbeats of different rates within the phantom 100 using the same equipment that will be used on patients in a clinical setting.

Altogether, the phantom 100 of FIGS. 1-3 includes organ structures that may be imaged using standard ultrasound equipment that is identical to that which is used on patients in clinical settings and, indeed, might be the same equipment in some embodiments. This enables a health care professional to practice locating structures within the phantom 100 using the same clinical equipment that will be used on patients.

According to other embodiments, and as would be appreciated by those of ordinary skill in the art having the benefit of the disclosure provided herein, manipulations of pressure bulb 112 may be varied to simulate various heart conditions of a fetus, such as an arrhythmia.

Figure 4:
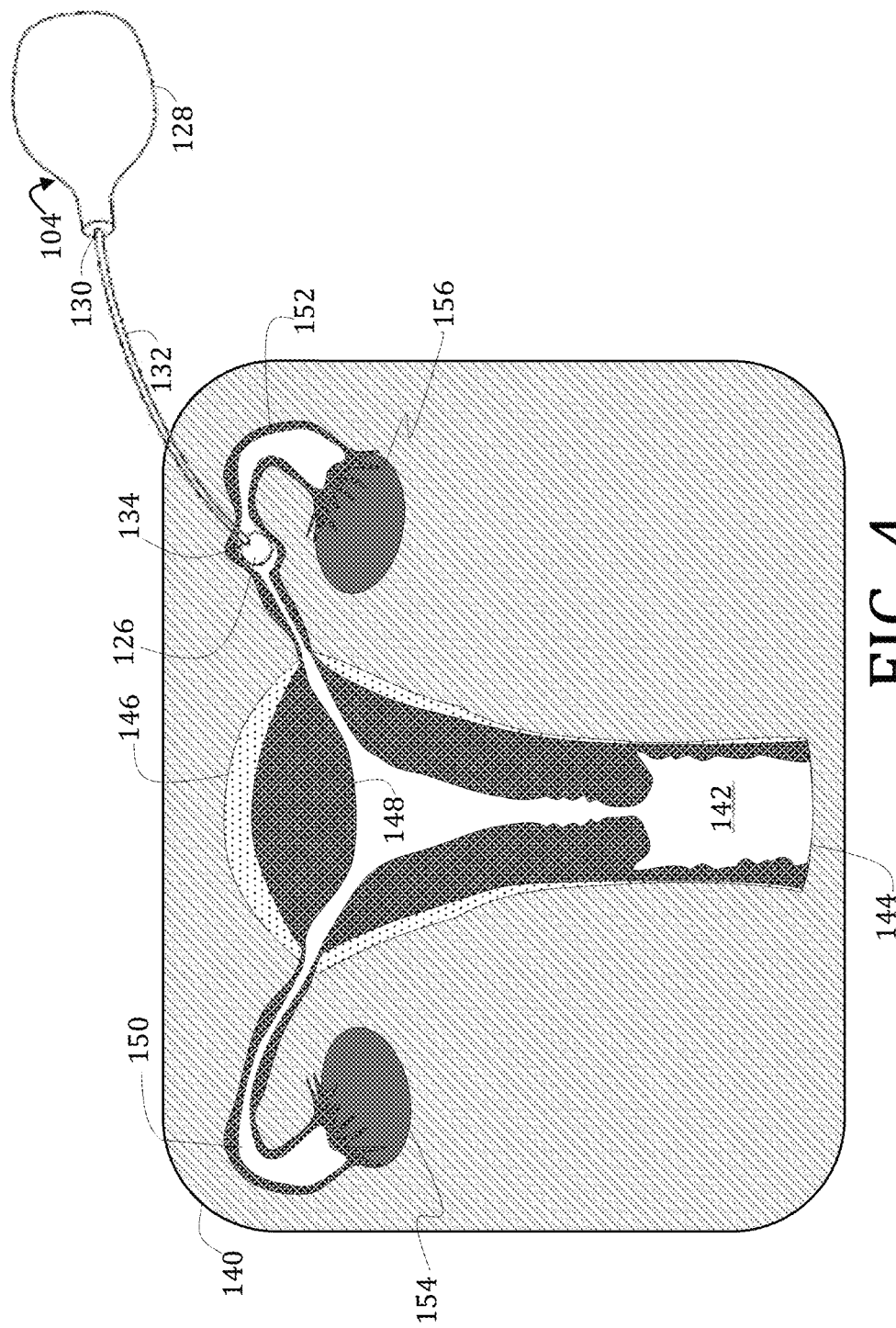
FIG. 4 is an axially-directed, cross-sectional view of an ultrasound phantom according to another embodiment of the present invention.

It would be further understood by the skilled artisan that various pregnancy conditions may be simulated, such as a viable pregnancy, an aborted pregnancy, an ectopic pregnancy, a twin gestation, or the like. In that regard, and with reference now to FIG. 4, an axially-directed cross-section of a replaceable section 140 according to another embodiment of the present invention is shown. Structures provided within the illustrative replaceable section 140 include a vaginal canal 142, a cervix 144, a uterus 146, a thickened uterine wall 148, Fallopian tubes 150, 152, and ovaries 154, 156. As shown, a fetus 158 is disposed outside of the uterus 146 and within the Fallopian tube 152, so as to simulate an ectopic pregnancy. Although not specifically illustrated, in yet another embodiment no fetus may be present so as to simulate a negative pregnancy. Still other embodiments may include multiple fetal structures to simulate the possibility of multiple embryos. When multiple fetal structures are present, the fetal heartbeat simulator may include a plurality of tubes with each tube being received by a respective one of the fetal structures. Alternatively, a plurality of fetal heartbeat simulators, corresponding to the number of fetal structures, may be used. The fetal heartbeat simulators may be operated to simulate different heart rates.

In yet other embodiments not specifically illustrated herein, the housing having a single, large cavity and a removable cover. In this way, anatomical structures within the phantom may be moved about within the cavity, removed, or replaced in a manner similar to that described above with respect to the replaceable section. These various configurations provide for a wider range of training scenarios for the health care professional.

Figure 5:
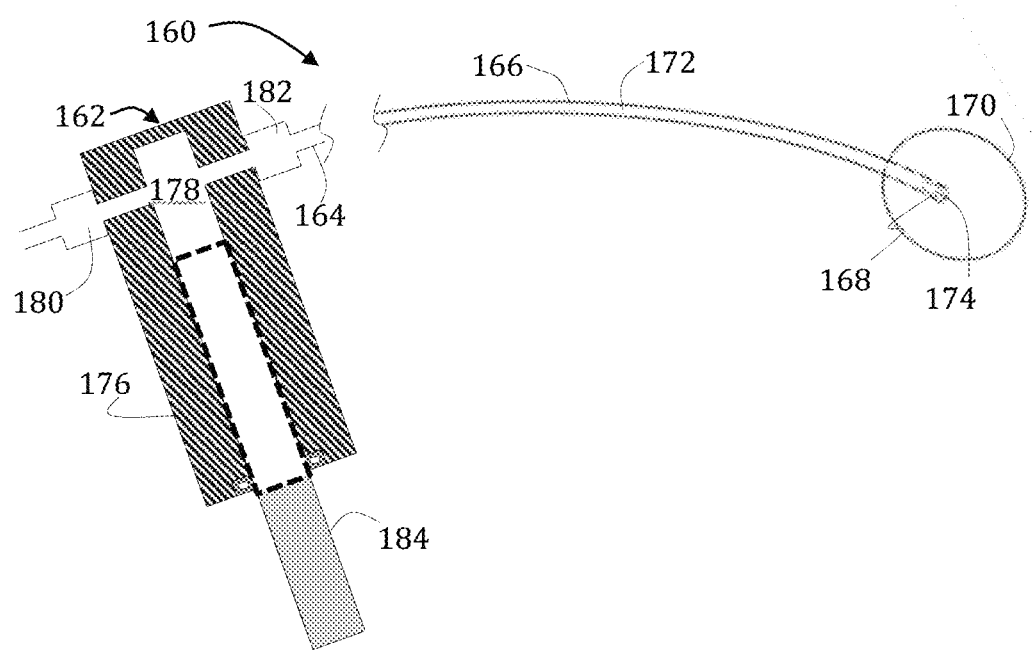
FIG. 5 is a side elevational views of fetal heartbeat simulators according to another embodiment of the present invention.

Referring now to FIG. 5, a fetal heartbeat simulator 160 according to another embodiment of the present invention is described and includes a pressure mechanism (illustrated in this figure as a reciprocating pump 162) operably coupled to a proximal end 164 of a tube 166 (which may, again be a 6 Fr catheter, for example). A distal end 168 of the tube 166 may be configured to be received by, or operably coupled to, the fetus 170, if present.

Similar to the embodiment described above, the tube 166 may be sealed at the distal end 168 and be filled with at least two fluids 172, 174 with the second fluid 174 (represented as a bubble) being restricted to the distal end 168 of the tube 166.

The reciprocating pump 162 may include a body having an internal fluid cavity with an inlet and outlet in fluid communication therewith. A piston moves with respect to the body into (shown in phantom) and out of (shown in solid) the fluid cavity. In use, movement of the piston out of the fluid cavity releases pressure from the first and second fluids 172, 174 within the tube such that the bubble of the second fluid 174 expands. Selective movement of the piston into the fluid cavity increases pressure on the first and second fluids 172, 174 within the tube such that the bubble of the second fluid 174 contracts. Displacement of the piston may be manual or operated by a controller (not shown).

The embodiment of FIG. 5 may offer certain advantages, such as greater control and regulation of the simulated fetal heartbeat. Additionally, in some embodiments the reciprocating pump 162 may be incorporated into the housing 102 (FIG. 1) so as to create a unitary phantom structure. Accordingly, a controller may be operably coupled (wired or wireless) to the pump 162 for operation thereof.

Figure 6:
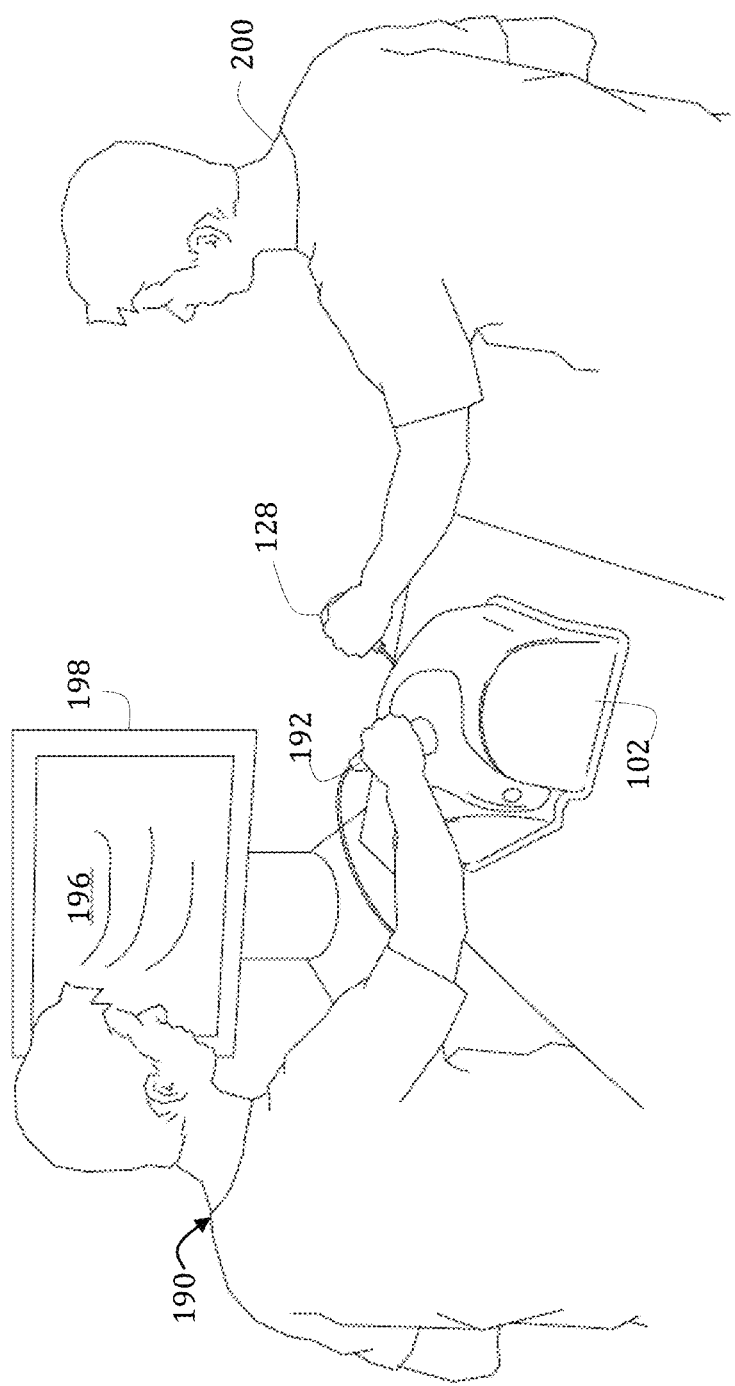
FIG. 6 depicts an exemplary health care professional training session employing an ultrasound phantom according to an embodiment of the present invention.

An exemplary training session using the phantom illustrated in FIGS. 1-3 is shown in FIG. 6. A health care trainee 190 is using a conventional, transabdominal ultrasound probe 192 of a clinical ultrasound apparatus (not shown) to generate an ultrasound image 196 of the fetus 126 (FIG. 1) on a display 198. A trainer 200 selectively actuates the pressure bulb 128 of the fetal heartbeat simulator 104 during the training session to simulate a desired scenarios of fetal heart rate. Because of the construction of the phantom 100, specialized training apparatus and equipment is not required.

Figure 7:
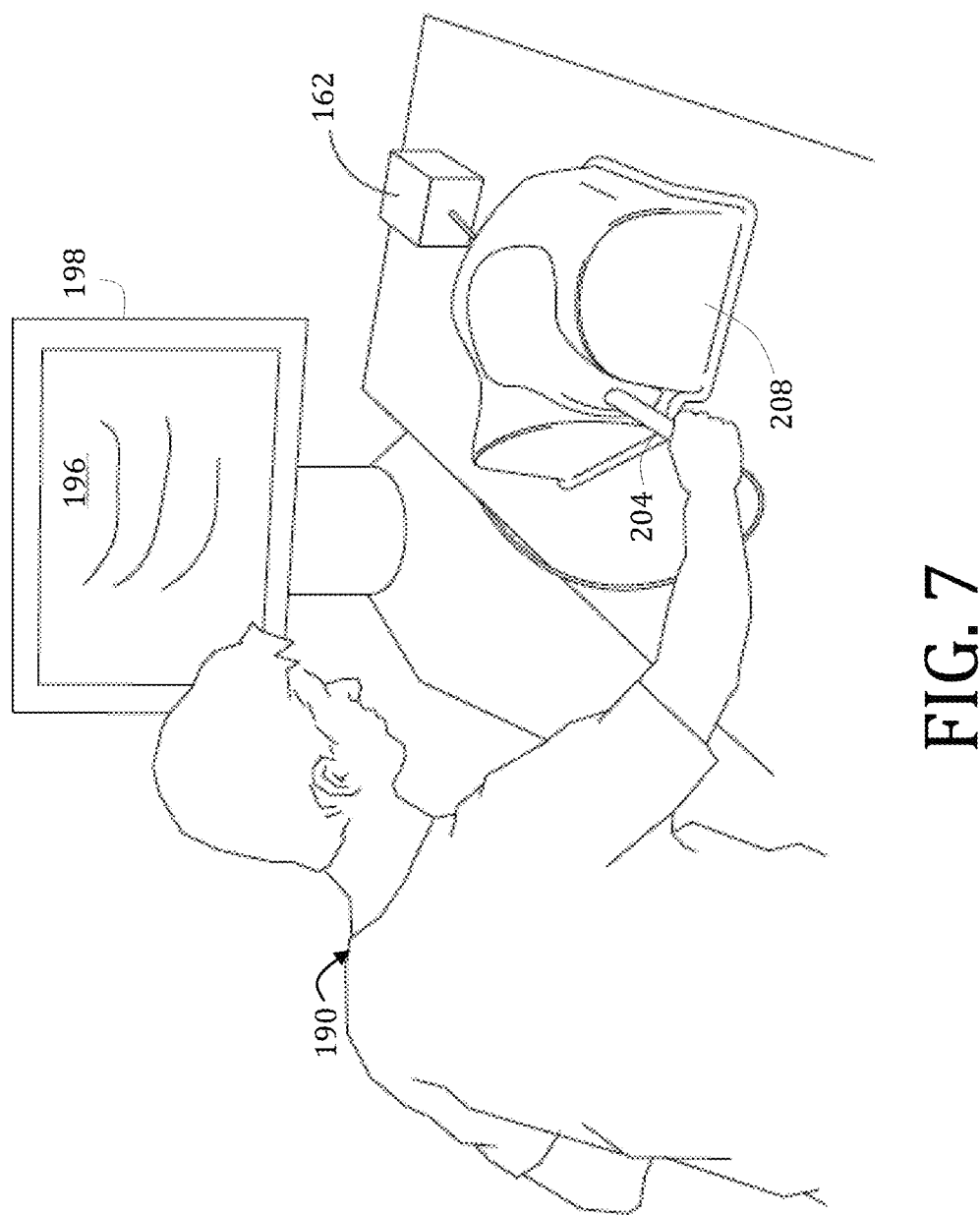
FIG. 7 depicts an exemplary health care professional training session employing an ultrasound phantom according to another embodiment of the present invention.

Another exemplary training session according to another embodiment of the present invention is shown in FIG. 7. Here, the health care trainee 190 is using a conventional, transvaginal ultrasound probe 204 of the clinical ultrasound apparatus (not shown) to generate an ultrasound image 206 on the display 198. The housing 208 of the phantom illustrated in FIG. 7 is similar to the housing 102 described with reference to FIG. 1 while the fetal heartbeat simulator 160 is that which is illustrated in FIG. 5. In this embodiment, the trainee 190 may test his/her skills without a trainer 200. Moreover, the trainee 190 may not only test his/her ability to detect fetal heartbeat but, by adjusting a speed control of the reciprocating pump, test his/her ability to identify and diagnose one or more obstetric conditions.

The consistency that is developed with the clinical ultrasound equipment used by the health care professional helps improve performance when the health care professional moves from training on the phantom to live patient care, because he will be using the same ultrasound equipment and thus will be more familiar with the ultrasound equipment. This will allow the health care professional to put more attention on the patient and on the exam, instead of on the use of the ultrasound equipment.

Thus, various embodiments of the phantom according to the present invention are able to demonstrate fetal heart activity, which allows for teaching a broader range of clinical scenarios.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A phantom comprising:
    a housing comprising an exterior substantially shaped like a female human pelvic region and surrounding an interior; and
    a fetal heartbeat simulator comprising:
        a tube having distal and proximal ends, the distal end being positioned within the interior of the housing;
        a first fluid having a first compressibility and filling the tube;
        a second fluid having a second compressibility that is greater than the first compressibility, the second fluid being disposed within the distal end of the tube; and
        a pressure mechanism operably coupled to the proximal end of the tube and configured to selectively compress and decompress the first and second fluids.

2. The phantom of claim 1, further comprising:
    a fetal structure positioned within the interior of the housing, the distal end of the tube being operably coupled to the fetal structure.

3. The phantom of claim 2, wherein the fetal structure is substantially the size of an eight-week-old human fetus.

4. The phantom of claim 2, wherein the housing further comprising:
    a uterus structure disposed within the interior, the fetal structure being positioned within the uterus structure.

5. The phantom of claim 1, wherein the second fluid is air and the first fluid is water.

6. The phantom of claim 1, wherein the pressure mechanism is a hand-operated pressure bulb or a reciprocating pump.

7. The phantom of claim 1, the fetal heartbeat simulator further comprising:
    a controller operably coupled to the pressure mechanism and configured control the selective compression and decompression of the first and second fluids.

8. The phantom of claim 1, wherein the housing further comprising:
    a bladder structure within the interior, a bowel structure within the interior, or both.

9. The phantom of claim 1, wherein the housing further comprising:
    a uterus structure disposed within the interior; and
    a Fallopian tube structure disposed within the interior and coupled to the uterus structure.

10. The phantom of claim 9, wherein the distal end of the tube is operably coupled to the uterus.

11. The phantom of claim 9, wherein the distal end of the tube is operably coupled to the Fallopian tube.

12. A method of training a health care professional to find a fetal heartbeat using the ultrasound phantom of claim 1, the method comprising:

operating an ultrasound transducer on the exterior of the phantom;

actuating the pressure mechanism to simulate a fetal heartbeat; and detecting the selective compression and decompression of the first and second fluids.

13. The method of claim 12, wherein actuating the pressure mechanism includes operating a pressure bulb or a reciprocating pump.

14. A fetal heartbeat simulator comprising:
a fetal structure;
a tube having distal and proximal ends, the distal end being within the fetal structure;
a first fluid having a first compressibility and filling the tube;
a second fluid having a second compressibility that is greater than the first compressibility, the second fluid being disposed within the distal end of the tube; and
a pressure mechanism operably coupled to the proximal end of the tube and configured to selectively compress and decompress the first and second fluids.

15. The fetal heartbeat simulator of claim 14, wherein the fetal structure is substantially the size of an eight-week-old human fetus.

16. The fetal heartbeat simulator of claim 14, wherein the second fluid is air and the first fluid is water.

17. The fetal heartbeat simulator of claim 14, wherein the pressure mechanism is a hand-operated pressure bulb or a reciprocating pump.

18. The fetal heartbeat simulator of claim 14, further comprises:
a controller operably coupled to the pressure mechanism and configured control the selective compression and decompression of the first and second fluids.

* * * * *